United States Patent [19]
Gillies

[11] Patent Number: 5,149,635
[45] Date of Patent: Sep. 22, 1992

[54] MESSENGER RNA STABILIZATION IN ANIMAL CELLS

[75] Inventor: Stephen D. Gillies, Scituate, Mass.
[73] Assignee: Abbott Biotech, Inc., Needham Heights, Mass.
[21] Appl. No.: 523,255
[22] Filed: May 16, 1990

Related U.S. Application Data

[63] Continuation of Ser. No. 907,067, Sep. 12, 1986, abandoned.
[51] Int. Cl.⁵ .................. C12P 21/02; C12N 15/85; C12N 5/10; C12N 15/00
[52] U.S. Cl. .................. 435/69.1; 435/320.1; 435/172.3; 435/240.2; 935/34; 935/60; 935/70
[58] Field of Search ............... 435/69.1, 320.1, 240.2

[56] References Cited

U.S. PATENT DOCUMENTS

| | | | |
|---|---|---|---|
| 4,624,926 | 11/1986 | Inouye et al. | 435/252.33 |
| 4,663,281 | 5/1987 | Gillies | 435/69.1 |
| 4,666,848 | 5/1987 | Gelfand et al. | 435/252.3 |
| 4,675,285 | 6/1987 | Clark et al. | 435/6 |
| 4,769,238 | 9/1988 | Rutter et al. | 424/89 |

FOREIGN PATENT DOCUMENTS 0077689 10/1982 European Pat. Off. .

OTHER PUBLICATIONS

Karasuyama et al, Eur. J. Immunol., vol. 18, pp. 97-104, (1988).
Khoury, G. et al, Cell, vol. 33, pp. 313-314, Jun., 1983.
Proc. Nat. Acad. Sci. USA, vol. 80, pp. 825-829, Feb., 1983 Immunology—Vernon T. Oi et al, Immunoglobulin Gene Expression.
Nature, vol. 301, issued 1983, Jan. pp. 214-221, D. Pennica et al Cloning and Expression of Human Tissue-Type Plasminogen Activator cDNA in E. coli.
Nature, vol. 263, issued 1976, Sep., pp. 211-214, N. Proudfoot et al Non-Coding Region Sequences in Eukaryotic Messenger RNA.
Gillies et al., "A Tissue-Specific Transcription Enhancer Element is Located in the Major Intron of a Rearranged Immunoglubulin Heavy Chain Gene", Cell 33, 717-728, 1983.
Soreq et al., "Translational Activity and Functional Stability of Human Fibroblast $B_1$ and $B_2$ Interferon mRNA's Lacking 3'-Terminal RNA Sequences", Proc. Natl. Acad. Sci., USA, 78, 1741-1745, 1981.
Zaret et al., "Mutationally Altered 3' Ends of Yeast CYC1 mRNA Affect Transcript Stability and Translational Efficiency", J. Mol. Biol., 176, 107-135, 1984.
Kozak, "Compilation and Analysis of Sequences from the Translational Start Site in Eukaryotic mRNA's", Nucleic Acids Res., 12, 857-871, 1984.
Yamaguchi et al., "Relationship Between Structure of the 5' Noncoding Region of Viral mRNA and Efficiency in the Initiation Step of Protein Synthesis in a Eukaryotic System", Proc. Natl. Acad. Sci., USA, 79, 1012-1016, 1982.
Hsu and Schimmel, "Yeast LEU1, Repression of mRNA Levels by Leuane and Relationship at 5'-Noncoding Region to that of LEU2", J. Biol. Chem., 259, 3714-3719, 1984.
Baralle, "The Function of Significana of Leader and Trailer Sequences in Eukaryotic mRNA's", Int. Rev. Cytol., 81, 71-106.
Ross and Pizarro, "Human Beta and Delta Globin Messenger RNA's Turn Over at Different Rates", J. Mol. Biol., 167, 607-617, 1983.
Shaw and Kamen, "A Consered AU Sequence from 3' Untranslated Region of GM-CSF mRNA Mediates Selective mRNA Degration", Cell, 46, 659-667, 1986.

Primary Examiner—Richard A. Schwartz
Assistant Examiner—S. L. Nolan
Attorney, Agent, or Firm—Testa, Hurwitz & Thibeault

[57] ABSTRACT

Disclosed is a method of increasing production of proteins, e.g., human tPA, in mammalian cells which normally secrete immunoglobulins. Degradation of mRNA transcribed from recombinant DNA is decreased by decreasing the length of the untranslated region of the mRNA. The untranslated region of DNA encoding a protein of interest is altered to produce a shorter recombinant DNA having an untranslated region comprising a poly A addition signal (AATAAA) and less than about 300 nucleotide bases interposed between said poly A signal and the stop codon 3' of the coding region of the gene of interest. The mammalian cell line is transfected and cultured to produce greater amounts of the protein of interest than the same cell line transfected with the unaltered DNA.

28 Claims, 2 Drawing Sheets

MESSENGER RNA STABILIZATION IN ANIMAL CELLS

This application is a continuation of application Ser. No. 907,067, filed Sep. 12, 1986, now abandoned.

BACKGROUND OF THE INVENTION

This invention relates to products and methods for increasing production of proteins in mammalian cells of lymphoid origin. More particularly, it relates to products and methods for increasing protein production by increasing the steady state level of translatably competent mRNA by decreasing the rate of intracellular degradation of the mRNA.

Protein production in most animal cells includes synthesis of enzymes, structural proteins, surface proteins, and numerous proteins having specialized functions such as lymphokines and hormones. Typically, relatively modest amounts of these proteins are produced. There are, however, types of animal cells which are capable of producing and secreting large amounts of proteins for systemic use in the animal body. Examples of the latter type of cells include cells of the circulatory system which produce globulins and fibrinogen, liver cells which produce serum albumin, and the beta cells of Islets of Langerhans which produce insulin. If the genetic mechanisms responsible for such high level expression could be exploited to produce lymphokines, antibodies, or other proteinaceous materials of interest, large supplies of valuable proteins could be made available.

Expression of endogenous DNA in eucaryotic cells involves transcription of the DNA into mRNA, subsequent migration of the mRNA to ribosomes followed by tRNA-mediated translation of the mRNA into proteins comprising the sequence of amino acids encoded by the mRNA between its start and stop signal codons.

As disclosed by Gillies et al in Cell, Vol. 33, pp. 717-728, July, 1983, and in co-pending U.S. application Ser. No. 592,231, filed Mar. 22, 1984, now U.S. Pat. No. 4,663,2 cellular enhancer elements play an important role in the high level expression of protein in specialized cells which produce large amounts of immunoglobulin. The enhancers appear to function by increasing the rate of DNA transcription into mRNA by endogenous mRNA polymerase. Increased concentrations of mRNA result in significant increases in the level of expression in such cells. The activity of such enhancer elements is independent of orientation and can be observed even when the sequence comprising the enhancer is located 10,000 base pairs or more away from the promoter for the gene encoding the protein. These cellular enhancers appear to be tissue specific, i.e., the activity of a cellular enhancer which functions in the endogenous genome of a lymphoid cell to increase production of a particular mRNA is greatly decreased or absent if the enhancer is incorporated in a vector used to transform non-lymphoid cells. However, a vector including the enhancer element, promotor, and a recombined gene encoding a desired protein, if transfected into a cell of the same type as that in which the enhancer naturally increases the transcription rate, can successfully transform the cell to express the recombined gene at high levels.

Eucaryotic DNA's comprise a sequence of bases beyond the stop signal, a portion of which serve as a signal to initiate addition of adenine residues (hereinafter poly A) 3' of the stop signal in the translated mRNA. The polyadenylation occurs mainly in the nucleus and is mediated by poly A Polymerase that adds one adenylic acid residue at a time. Poly A does not code for an amino acid sequence after the stop codon has terminated translation, but is thought to contribute to stabilization of mRNA's and to the efficiency of translation of the mRNA coding region into amino acids.

The poly A in the mRNA of mammalian cells lies in a sequence known as the 3'untranslatable (hereinafter 3'UT) end portion. The 3'UT typically extends from the termination codon for the translation product to the terminus of the poly A. The 3'UT regions of mammalian mRNA's typically have an area of homology, known as the AAUAAA hexanucleotide sequence. This sequence is thought to be the poly A addition signal. It often precedes by 11 to 30 bases the poly A addition site.

The function, if any, of the 3'UT and poly A region has been investigated recently by Soreq et al. (Proc. Natl. Acad. Sci. U.S.A. Vol. 78, No. 3, pps. 1741-1745, March, 1981); Zaret et al. (J. Mol. Biol., 1984 Vol. 176, pp. 107-135); Baralle (International Review of Cytology, Vol. 81, 1983, pp. 71-106); and Ross et al. (J. Mol Biol., 1983, Vol. 167, pp. 607-617).

Soreq et al. reported that removal of the poly A and approximately 100 adjacent residues from a first human fibroblast beta interferon mRNA did not alter the translational activity or the functional stability of this mRNA in oocytes, whereas the deletion of the poly A and approximately 200 adjacent residues did decrease its translational efficiency. The removal of approximately 200 poly A residues and 200 adjacent residues from a second beta interferon mRNA did not alter either the translational activity or functional stability of the mRNA in oocytes. These authors concluded that neither the poly A residues nor large segments of the 3' noncoding region are required for the maintenance of the functional stability of human beta interferon mRNAs in such oocytes.

Zaret et al studied the cyc 1-512 mutant of the yeast *S. cerevisiae* which contains a 38 base pair deletion in the 3' noncoding region of the CYC-1 gene which encodes iso - 1 - cytochrome c. They reported that different 3' noncoding sequences which arose by chromosomal rearrangement increased the stability of CYC-1 mRNA and have varying effects upon the mRNA translational efficiency.

In Baralle's publication, *The Functional Significance of Leader and Trailer Sequences in Eucaryotic mRNAs*, the author reported that there is "no obvious function for the 3' non coding region" and that "the occurrence of sizable deletions or insertions during evolution of these genes suggests that the particular sequences which comprise the 3' non coding region are not essential to mRNA function." Baralle reported however that poly A does have a role in promoting mRNA stability. For instance, it has been found that removal of the poly A segment from globin mRNA greatly decreases the half-life of the mRNA in oocytes. However, Baralle suggests that poly A is apparently not necessary for successful translation as has been demonstrated by studies wherein the poly A has been removed from the mRNA.

Ross and Pizarro studied the hypothesis that steady state levels of human beta and delta globin Proteins are determined in part by the intracellular stability of their respective messenger RNAs. They found that the rapid turnover of delta globin in mRNA accounts, at least in part, for the low level of delta globin mRNA in non nucleated peripheral blood reticulocytes, and speculated that the rate of mRNA decay may be determined by nucleotide sequence signals located in the 3' untranslated region. They observed that the 5' untranslated regions of beta and delta globin mRNAs are similar, but that their 3' untranslated regions differ significantly, and proposed that it should be possible to test the role of the 3' untranslated region in determining mRNA stability by comparing the half lives in transfected cells of chimeric mRNAs containing beta or delta 3' termini.

European Patent 0077689 discloses a method of gene manipulation wherein a yeast is transformed with a gene in which the 3'UT of a structural gene is added downstream from an exogenous gene. The transformant reveals a higher level of expression when the exogenous gene includes the 3'UT. In fact, studies revealed that the expression in the yeast carrying the plasmid with the region corresponding to the 3'UT as added is about 10-fold as compared with the yeast carrying the plasmid with no such region added.

It is an object of this invention to provide a product and process for efficient production of a desired protein including human tPA in certain types of animal cells. Another object is to provide vectors for transfecting animal cells to induce high level expression of a gene encoding a desired protein. Another object is to provide transformants which when cultured produce large amounts of protein for therapeutic, diagnostic, and related uses. Still another object of the invention is to provide methods and recombinant DNAs which promote mRNA stability in transfected cell lines by reducing the rate of intracellular mRNA decay, thereby increasing levels of expression.

These and other objects of the invention will be apparent to those skilled in the art from the following description and claims.

SUMMARY OF THE INVENTION

A process has now been discovered for increasing production of selected proteins in mammalian cell lines which normally secrete immunoglobulins. It has been found that a short segment of a 3'UT region and the polyadenylation region, if recombined 3' of the stop codon in a DNA coding for a protein of interest, are effective in promoting an increase in production of the protein of interest. The sequences comprising the small segment of 3'UT and the polyadenylation site appear to stabilize mRNA corresponding to the translated region and increase translation levels. The steady state level of the mRNA encoding the protein of interest is increased relative to mRNAs having longer untranslated regions.

In accordance with the invention, this discovery is exploited to provide vectors and processes for producing a protein of interest and to produce transformants which may be cultured to produce such materials at improved levels of expression. Either exogenous or endogenous proteins may be produced in accordance with the invention, i.e., one can produce proteins not encoded in the natural genome of the host cells, proteins which are encoded but not normally expressed in the host cells, or proteins which normally are expressed only at low levels.

In accordance with the invention, a DNA including a coding region, a stop signal codon, and a native 3'UT including a polyadenylation signal for the protein of interest is derived from a cell which naturally produces the protein of interest. The nucleotide sequence of the 3'UT region of this DNA is altered to produce an intact, transcriptionally competent, shorter recombinant DNA having an altered 3'UT having less than about 300 nucleotide bases between the stop signal and the AA-TAAA polyadenylation signal. The recombinant DNA is transfected into a selected mammalian cell line which normally secretes immunoglobulins. The resulting transfected cell line is cultured to produce the protein of interest. The amount of protein produced is greater than that of the same cell line containing unaltered DNA for the protein of interest containing the longer native 3'UT.

In one embodiment, the shorter recombinant DNA contains a portion of the 3'UT of the DNA of the protein of interest, though the 3'UT from other DNA's may be used. In other embodiments, at least a portion of the altered 3'UT is obtained from a non-cellular DNA, e.g., viral DNA, while in others it is obtained from a mammalian DNA. The protein of interest may be an immunoglobulin or fraction thereof, a hormone, vaccine, lymphokine, cytokine, enzyme or pro-enzyme. For instance, the desired proteins may comprise a plasminogen activator such as human tissue plasminogen activator, the production of which is used as a model herein and described in detail. The mammalian cell line is a culturable cell line such as a myeloma cell line, though other mammalian cells which normally secrete immunoglobulins may be used.

In accordance with the invention, the process may comprise the additional step of combining proximate the DNA encoding the protein of interest, a DNA comprising a cellular enhancer element to enhance transcription of the recombinant DNA. The invention may further feature a blocking element as described in copending application Ser. No. 837,595 filed Mar. 7, 1986 now abandoned. Such blocking elements enable production of transformants which produce high levels of a desired protein while producing the marker protein only at levels required for selection.

The invention further features a vector for producing a protein when transfected into a mammalian cell line that normally secretes immunoglobulins. The vector is composed of transcriptionally competent DNA produced in accordance with the above summarized process. This vector operates to produce increased quantities of the desired protein relative to otherwise identical vectors having a 3'UT region native to the gene encoding the protein of interest.

The invention further features a transformant for producing a protein of interest. The transformant preferably comprises a mammalian cell which normally produces immunoglobulins such as a myeloma cell. The transformant contains the vector harboring the expressable DNA summarized above. The transformant is capable of producing increased quantities of the protein of interest relative to otherwise identical transformants containing recombinant DNA including the 3' untranslated region native to the gene encoding the protein of interest.

The enhanced expression levels produced in accordance with the invention are apparently caused by an increase in the steady state level of corresponding mRNA in transfected cells. It is believed that the shortness of the 3'UT region of the fused mRNA serves to reduce degradation of the mRNA within the cell, thereby increasing the intracellular half-life of the mRNA, and increasing expression levels.

It is known that phosphodiester bridges of DNA and RNA are attacked by exonucleases which act on either the 3' or 5' end of the molecule. Enzymes which act on the 3' end hydrolyze the ester linkage between the 3' carbon and the phosphoric group, while the 5' enzymes hydrolyze the ester linkage between the phosphoric group and the 5' carbon of the phosphodiester bridge. Endonucleases do not require a free terminal 3' or 5'-hydroxyl group; they attack 3' or 5' linkages wherever they occur in the polynucleotide chain.

It is hypothesized that recombinant DNAs comprising a long 3'UT are digested when an endonuclease cleaves a portion of the mRNA of the 3' UT not bound by a ribosome, followed by exonuclease digestion. Because of the shortness of the 3'UT region of the mRNA, when it associates with the ribosomes, less mRNA is left unbound to ribosomes and the number of sites for endonuclease attack are reduced. The presence of the poly A site protects the 3' end from exonucleases. The rate of degradation of mRNA is therefore decreased due to the shortness of the 3'UT region. Therefore, by the mechanism of the invention, mRNA is stabilized and its biological function increased to result in the increased expression of desired proteins.

For a fuller understanding of the nature and objects of the invention, reference should be made to the following detailed description and accompanying drawings.

DESCRIPTION OF THE INVENTION

The invention provides a method, vector and transformant for increasing production of selected proteins in mammalian cells. The 3'UT region of a DNA encoding a protein of interest is altered to produce a shorter recombinant DNA having an 3'UT region, generally comprising less than about 300 nucleotide bases and may comprise less than 200 bases between the stop codon of the gene and the AATAAA poly A signal. A mammalian cell line which normally produces and secretes immunoglobulins is transfected with the resultant recombinant DNA. The transformant is cultured to produce increased amounts of the protein of interest as compared with the same cell line transfected with an unaltered 3'UT region.

Figure 1:
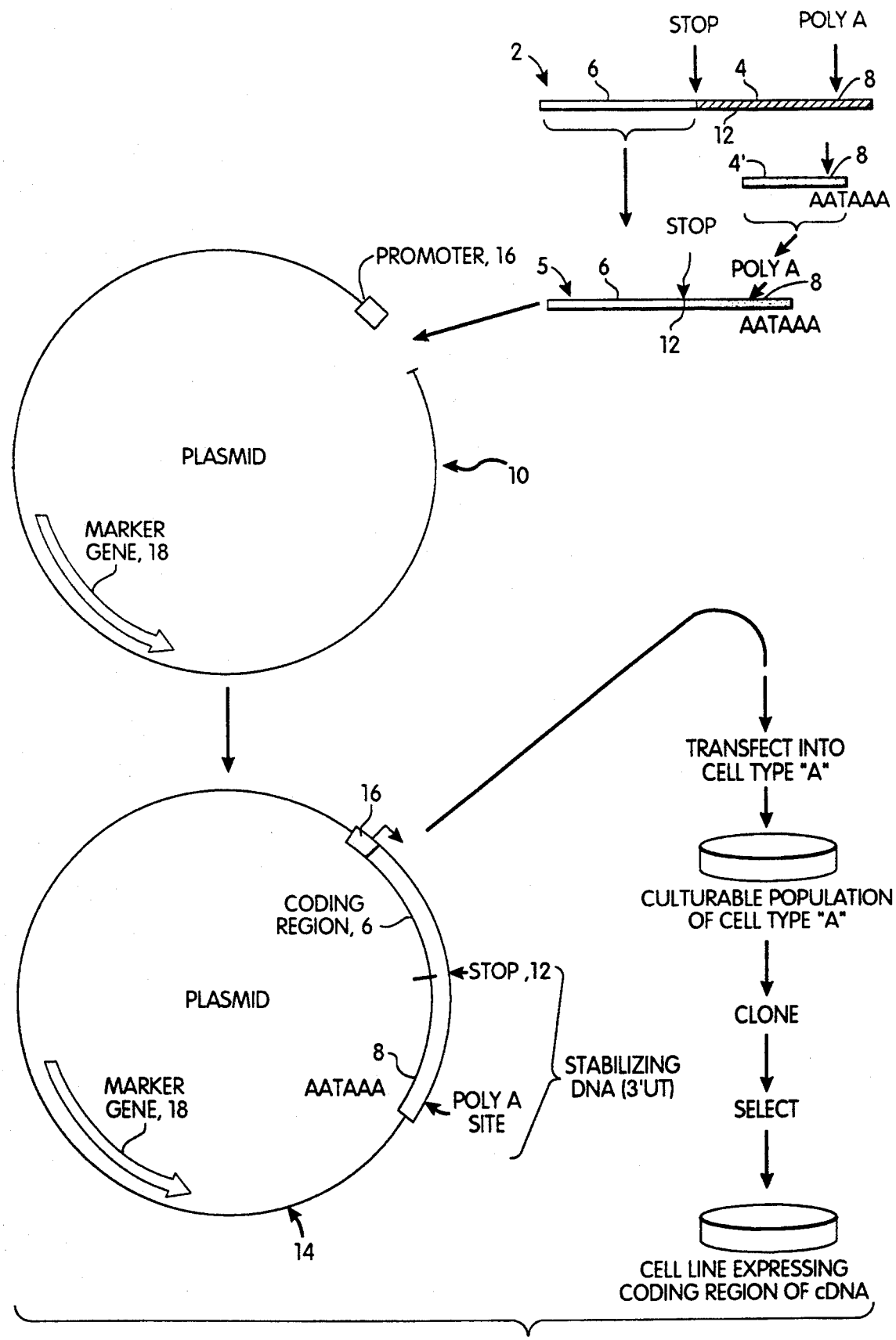
FIG. 1 is a schematic diagram illustrating the overall procedure of the invention.

The process of the invention is represented in FIG. 1. DNA 2 comprises a coding region 6 which encodes a protein of interest. It is derived from a cell which naturally produces the protein, e.g., synthesized by conventional techniques with knowledge of the DNA sequence. For instance, the DNA may be a naturally occurring DNA or a chemically synthesized DNA. Alternatively, the DNA may be a reverse transcribed cDNA derived by conventional cDNA techniques. The typically long nucleotide sequence of the untranslated region 4 of this DNA 2 is altered to produce an intact, transcriptionally competent, shorter recombinant DNA 5 including the region 6 encoding the protein of interest, and beyond the stop signal; a 3'UT (7) less than about 300 nucleotide bases long linked to a polyadenylation addition signal 8. The recombinant DNA 5 therefore comprises a coding region for the protein of interest 6, a stop signal 12 and a shorter 3'UT designated 7 interposed between stop signal 12 and a poly A addition signal 8. The 3'UT including the Poly A site of the recombinant DNA may be obtained from the DNA 2 encoding the protein of interest by splicing out a segment of the 3'UT or from another DNA. The recombinant DNA 5 is inserted into a plasmid 10 to produce an expression vector 14. The plasmid includes a promoter sequence 16 and an expressable marker gene 18. A mammalian cell line is transfected with the recombinant DNA, cloned, and screened for a subpopulation of cells which have successfully incorporated and can express the gene 6. The transfected cell line is cultured to produce the desired Protein which is then isolated and purified.

It has been noted that the 3'UTs of the highly abundant immunoglobulin mRNA's in lymphoid cells which secrete immunoglobulins are relatively short (less than about 300 nucleotides), whereas the 3'UTs of several genes of interest not expressed in lymphoid cells are relatively long. For example, the UT region of tPA is approximately 800 nucleotides long (Pennica et al, Nature, V. 301, 214–231, Jan., 10=983), that of Factor VIII about 1800 nucleotides (Wood et al, Nature, V. 312, 330–337, Nov., 1984), and that of erythropoietin about 560 nucleotides long (Jacobs et al, Nature, V. 313, 806–810, Feb., 1985).

The recombinant DNA techniques for manufacturing expression vectors and transformants useful in this invention are well-known and developed. They involve the use of various restriction enzymes which make sequence-specific cuts in DNA to produce blunt ends or cohesive ends, DNA ligases, techniques enabling enzymatic addition of sticky ends to blunt-ended DNA molecules, cDNA synthesis techniques, synthetic probes for isolating genes having a particular function, assembly of oligonucleotides to produce synthetic DNAs, conventional transfection techniques, and equally conventional techniques for cloning and subcloning DNA.

Various types of vectors may be used such as plasmids and viruses including animal viruses and phages. The vector will normally exploit a marker gene 18 which imparts to a successfully transfected cell a detectable phenotypic property which can be used to identify which individuals of a population of cells have successfully incorporated the recombinant DNA of the vector 14. Preferred markers for use in the myeloma cell lines comprise DNAs encoding an enzyme normally not expressed (or expressed only at low levels) by the cells which enable the cells to survive in an medium containing a toxin. Examples of such enzymes include thymidine kinase (TK), adenosine phosphoribosyltransferase (APRT), and hypoxanthine phosphoribosyl transferase (HPRT), which enable TK, APRT, or HPRT-deficient cells, respectively, to grow in hypoxanthine/aminopterin/thymidine medium; dihydrofolate reductase (DHFR), which enables DHRF-deficient cells to grow in the presence of methotrexate; the E.coli enzyme xanthine-guanosine phosphoribosyl transferase (XGPRT, the product of the gpt gene), which enables normal cells to grow in the presence of mycophenolic acid; and the procaryotic enzyme Tn5 phosphotransferase, which enables normal cells to grow in the presence of neomycin. Other suitable marker genes will be useful in the vectors used to transform myeloma cells in accordance with the invention.

Vectors of the invention may include an enhancer element of the type which acts on promoters disposed on both the 5' and 3' end of the enhancer element, or spaced apart from either end, to enhance transcription of genes located on the 3' end of the promotors. The enhancer element may include DNA of viral origin such as those disclosed by Banerji et al (Cell, V. 27, 299-308, 1981), deVilliers and Shaffner (Nucl. Acids Res., V. 9, 6251-6264, 1981), or Levinson et al. (Nature, V. 295, 568-572, 1982), but preferably is a cellular enhancer element of the type recently discovered by Gillies and Tonegawa and disclosed in Cell, (V. 33, 717-728, 1983), and in more detail in copending U.S. application Ser. No. 592,231, filed Mar. 22, 1984. The vector may further include a blocking element as described in copending application Ser. No. 837,595 filed Mar. 7, 1986, which enables production of transformants which produce high levels of a desired protein under the influence of the enhancer while producing the marker protein only at lower levels required for selection.

Figure 3:
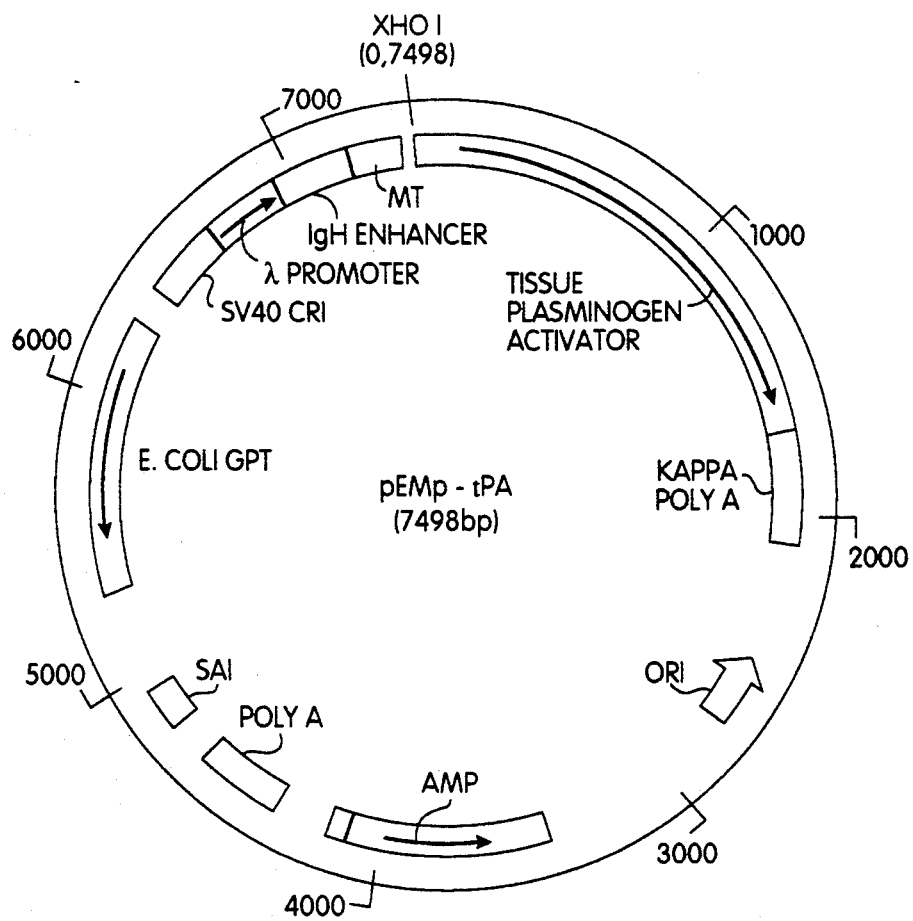
FIG. 3 is a diagram of plasmid pEMp-tPA, the preferred expression vector for use in the manufacture of tPA in myeloma cells. This vector represents the currently preferred embodiment of the invention.

FIG. 3 represents the restriction map of the preferred plasmid vector used for the production of tPA in accordance with the invention. This vector is designated pEMp-tPA and comprises 7498 base pairs. It includes a myeloma cell-derived enhancer element which enhances transcription of mRNA from inserted DNA encoding protein, here human tPA (see Gillies et al. *Cell.* 1983, supra), and exploits vector construction principles which regulate selectively the enhancer function in accordance with the disclosure of copending U.S. application Ser. No. 837,595. Details of the vector's constructions are disclosed below.

In preferred embodiments, the host cell system to be transfected with the recombinant DNA is a continuous or established cell line which has undergone a change enabling the cells to grow indefinitely. These cells therefore are unlike normal cells that divide in culture for a limited number of generations before senescing. The ability to grow indefinitely further assists in scaling-up production of proteins of interest.

The host cells used for the practice of the invention are mammalian cells that normally produce and secrete immunoglobulins. These cells normally reside in the circulatory system. The cell actually used may have lost the ability to secrete immunoglobulins through previous selection.

It is further preferred that the host system comprise murine or rat derived cells (as opposed to human cells) to reduce the possibility of contamination of product protein by human viruses. In preferred embodiments, myeloma cells constitute the host culture system. Myeloma cells are typically easily cultured and secrete expression products into the extracellular medium.

The vector disclosed in FIG. 3, and other suitable expression vectors, are used in accordance with the invention to transfect myeloma cells, preferably of murine origin, such as cell line J558 (ATCC-TIB 6), Sp2/0-Ag-(ATCC CRL 1581), and P3X63-Ag8.653 (ATCC CRL 1580). The preferred myeloma cell line is J558L (ATCC CRL 9132, See Oi et al. *Proc. Natl. Acad. Sci.*, USA, V. 80, p. 825 1983). These cells comprise malignant transformants of B cells from the circulatory system of the Balb/C mouse, and are derived from myeloid tissue.

The transformants of the cells of the type set forth above may be cultured in suspension or preferably within microcapsules in accordance with the Procedure disclosed in U.S. Pat. No. 4,409,331 to F. Lim. For ease of purification, and to promote post-secretion stability of the protein product, it is preferred that the cells be cultured in serum-free medium. The extracellular protein is harvested daily as medium is replaced. This approach has the advantage of producing the product free of contaminating proteolytic enzymes and other inactivating factors often present in bovine or equine sera. The preferred J558L cell secretes lambda light chain of immunoglobulin A in significant quantities. This and other contaminating proteins can be separated readily from the protein product.

The invention may be used to manufacture large amounts of valuable proteins in additions to tPA in cells genetically engineered as disclosed herein. Non-limiting examples include other plasminogen activators and proactivators, blood clotting factors, hormones, interferons, antibodies, enzymes and pro-enzymes, vaccines, and various lymphokines and cytokines.

The example which follows should be understood to be exemplary in all respects, providing a detailed disclosure of a tPA production protocol embodying the invention, and a disclosure of the best mode currently known of practicing the invention.

EXAMPLE

The Production of tPA-Producing Myeloma Transformants

The basic expression vector, designated pEMpl, was constructed from the following fragments: (a) a 2.25 PvuII-BamHI fragment from pSV2-gpt (Mulligan and Berg, Science; V. 209, 1422-1427, 1980) containing the SV40 enhancer and early region promoter, the *E. coli* gpt gene, the SV40 small tumor-antigen intervening sequence, and the SV40 transcription termination and polyadenylation signals; (b) a 2.3 kb pVuII-EcoRI fragment from PBR322 containing the ampicillinase gene and the bacterial origin of replication (Sutcliffe, Proc. Natl. Acad. Sci., USA, V. 75, 3737, 1978); (c) a 0.3 kb PvuII-EcoRI fragment containing an immunoglobulin heavy chain enhancer (Gillies et al, Cell, V. 33, p. 717-728, 1983); (d) a 0.25 kb SacI-BglII fragment containing the metallothioneine I promoter (Brinster et al, Nature, V. 296, 39-42, 1982); and (e) a 0.4 kb AvaII-HaeIII fragment from the 3'UT region of the immunoglobulin kappa light chain gene, which includes the polyadenylation signal (Max et al, J. Biol. Chem., V. 256, 5116-5120, 1981). These fragments were ligated together in a series of reactions according to well known methodologies (see, e.g., Maniatis et al, *Molecular Cloning: A Laboratory Manual,* Cold Spring Harbor, 1982).

The basic expression vector was used to construct a series of vectors expressing tPA. Designated pEMl-tPA-A, -B, and -C, these three vectors all contained the entire coding region of the tPA cDNA, but differed in their 3' untranslated regions as described below.

The cDNA for tPA was obtained by standard techniques (Maniatis, supra). TPA clones containing the entire coding region, and approximately 800 base pairs of the 3'UT region were identified and confirmed by nucleotide sequencing. The tPA cDNA was truncated at the Bgl II site approximately 400 base pairs downstream of the translation stop codon and inserted via Xho I linkers into the unique XhoI site in the basic vector. The tPA 3'UT region in this expression vector, pEMl-tPA-A, therefore was composed of approximately 400 base pairs of the native tPA 3' UT and 200 base pairs of the 3'UT region of the immunoglobulin kappa light chain gene.

In vector pEMl-tPA-B the bulk of the native tPA 3'UT was eliminated by cloning at the Sau 3A site located 34 base pairs downstream of the translation stop signal and joining to the 200 base pair 3'UT of the immunoglobulin kappa light chain gene.

Vector pEMl-tPA-C differed from pEMl-tPA-B in that the 3'UT region of the kappa light chain gene was replaced with an approximately 200 base pair fragment from the 3'UT region of the SV40 late genes.

Figure 2:
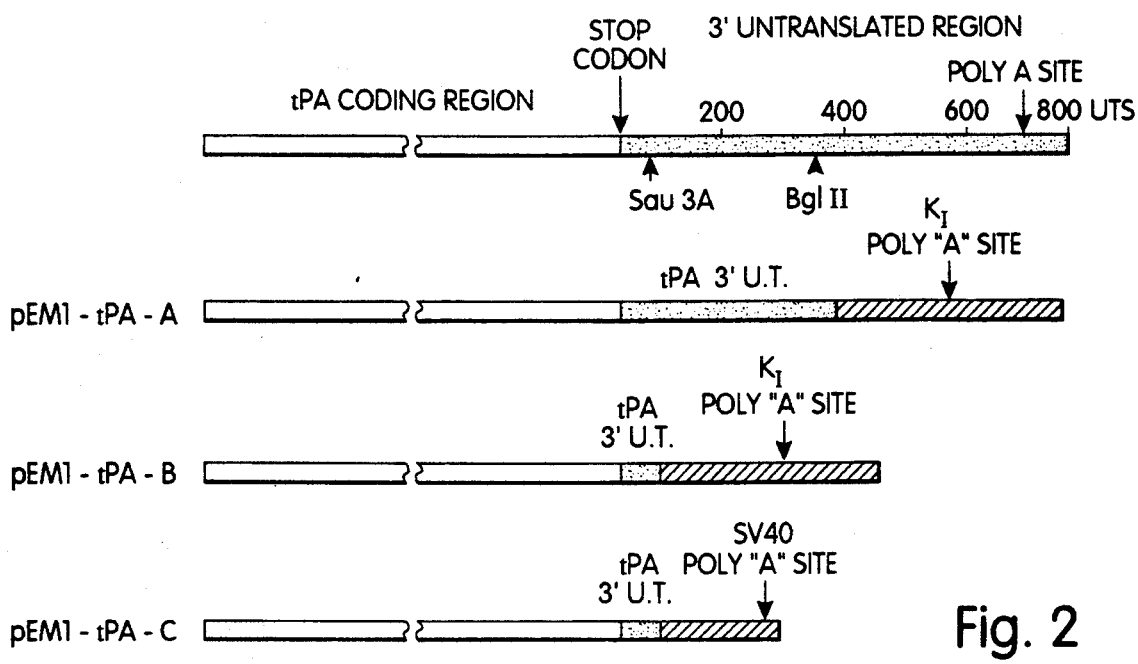
FIG. 2 is a diagram illustrating various segments of DNA fused with a gene encoding a desired protein product (tPA)

The recombinant tPA genes with the various 3'UT regions described above are depicted in FIG. 2. There is about 0.59 kb between the stop codon and the AATAAA polyadenylation signal in vector pEMl-tPA-A, 0.23 kb in pEMl-tPA-B, and 0.16 kb in pEMl-tPA-C.

The tPA-containing plasmids were transfected into J558L myeloma cells by the protoplast fusion method (Gillies et al, supra). Cells containing the plasmid, and therefore the gpt gene, were selected by culturing in media containing mycophenolic acid. Resistant colonies containing the plasmids were subcloned and screened for tPA expression. The synthesis and secretion of tPA into the medium was determined by means of an assay in which tPA converts plasminogen to plasmin, which then cleaves the chromogenic tripeptide S2251 (Pennica et al, supra). Because it is known that serum contains inhibitors of both tPA and plasmin (Collen and Lijnen, CRC Critical Reviews in Oncology/Hematology, V. 4, 249-301, 1986), transformants were cultures for 48 hours in serum-free medium before assay. Activity was measured in international units (IU) based on a standard supplied by the World Health Organization and confirmed by a tPA standard obtained from American Diagnostic, Inc.

No cloning expressing significant quantities of tPA could be found in the cells transfected with vector pEMl-tPA-A, although analysis indicated the presence of low levels of mRNA encoding tPA. Of 26 clones transfected with pEMl-tPA-B, 5 expressed tPA. If the highest expression level is given a relative value of 1.00, the expression of tPA by pEMl-tPA-B transfectants ranged between 0.28 and 1.00. Of 14 clones transfected with pEMl-tPA-C, 6 expressed tPA at a relative level of 0.12-0.44.

The invention may be embodied in other specific forms without departing from the spirit and scope thereof.

What is claimed is:

1. A process for producing a protein in a myeloma cell line, said process comprising the steps of:
   a) providing a recombinant DNA obtained from a cell which naturally produces said protein, said DNA comprising in sequence a coding region encoding said protein, a stop signal codon, and a native 3' untranslated region as it naturally occurs 3' to said coding region including a polyadenylation signal;
   b) reducing the number of base pairs of said native 3' untranslated region of said DNA between said stop signal and said polyadenylation signal to produce an intact, transcriptionally competent, shorter DNA having a shorter untranslated region comprising less than about 300 nucleotide bases between said stop signal codon and a polyadenylation signal;
   c) transfecting said myeloma cell line with said shorter DNA; and
   d) culturing said transferred cell line to produce said protein, the amount of protein produced by said transfected cell line being greater than the amount of protein produced by an otherwise identical cell line containing the DNA described in step a.

2. The process of claim 1 wherein said shorter untranslated region includes the sequence AATAAA, where A is adenine and T is thymine.

3. The process of claim 1, wherein said removing step further comprises
   ligating to said shorter native untranslated region a 3' untranslated region non-native to said coding region to produce a hybrid 3' untranslated region comprising less than about 300 nucleotide bases between said stop signal codon and a polyadenylation signal.

4. The process of claim 3 wherein said non-native untranslated region is obtained from a non-mammalian DNA.

5. The process of claim 4 wherein said non-native 3' untranslated region comprises the SV40 late gene 3' untranslated region.

6. The process of claim 3 wherein said non-native untranslated region is obtained from a mammalian gene.

7. The process of claim 6 wherein said non-native 3' untranslated region comprises an immunoglobulin light chain 3' untranslated region.

8. The process of claim 3 wherein said coding region encodes a plasminogen activator.

9. The process of claim 8 wherein said activator is human tissue plasminogen activator.

10. The process of claim 1 wherein said coding region encodes a protein selected from the group consisting of immunoglobulins, hormones, vaccines, lymphokines, cytokines, enzymes and pro-enzymes.

11. The process of claim 3 comprising the additional step of combining DNA comprising a cellular enhancer element proximate to said DNA encoding said protein to enhance transcription of said recombinant DNA.

12. The process of claim 5 or 7 wherein said coding region encodes a plasminogen activator.

13. A vector for producing a protein when transfected into a myeloma cell line, said vector comprising replicable, transcriptionally competent DNA having in sequence a first DNA segment comprising a promoter sequence, a second DNA segment encoding said protein, and a stop signal codon, and
   a third DNA segment 3' of said stop signal codon comprising a hybrid untranslated region comprising a sequence non-native to the gene encoding said protein and a polyadenylation signal, wherein said hybrid region comprises less than about 300 base pairs between said stop codon and said polyadenylation signal, said vector being operable to produce increased quantities of protein relative to otherwise identical vectors comprising the 3' untranslated region native to the gene encoding said protein.

14. The vector of claim 13 wherein said second DNA segment encodes a plasminogen activator.

15. The vector of claim 14 wherein said activator is human tissue plasminogen activator.

16. The vector of claim 13 wherein said third DNA segment includes the sequence AATAAA, where A is adenine and T is thymine.

17. The vector of claim 13 wherein said second DNA segment encodes a material selected from the group consisting of immunoglobulins, vaccines, lymphokines, cytokines, enzymes, and pro-enzymes.

18. The vector of claim 13 wherein said non-native 3' untranslated region comprises one of an SV40 late gene 3' untranslated region or an immunoglobulin light chain 3' untranslated region.

19. The vector of claim 18 wherein said second DNA segment encodes a plasminogen activator.

20. The vector of claim 13 wherein said third DNA segment is derived from the 3'UT of an immunoglobulin mRNA.

21. A transformant for producing a protein comprising a myeloma cell harboring expressible DNA comprising in sequence:
   a) a first DNA segment comprising a promoter sequence;
   b) a second DNA segment encoding said protein;
   c) a translational stop codon; and
   d) a third DNA segment 3' of said stop signal codon comprising a hybrid untranslated region comprising a sequence non-native to the gene encoding said protein and a polyadenylation signal, wherein said hybrid region comprises less than about 300 base pairs between said stop codon and said polyadenylation signal,
   said transformant being capable of producing increased quantities of protein relative to otherwise identical transformants containing recombinant DNA including the 3' untranslated region native to the gene encoding said protein.

22. The transformant of claim 21 wherein said non-native 3' untranslated region comprises one of the SV40 late gene 3' translated region or the immunoglobulin light chain 3' untranslated region.

23. The vector of claim 22 wherein said second DNA segment encodes a plasminogen activator.

24. The transformant of claim 21 wherein said third DNA segment is derived from the 3'UT of an immunoglobulin mRNA.

25. The transformant of claim 21 wherein said third DNA segment includes the sequence AATAAA, where A is adenine and T is thymine.

26. The transformant of claim 21 wherein said second DNA segment encodes and said transformant expresses a material selected from a group consisting of immunoglobulins, vaccines, lymphocytes, cytokines, hormones, enzymes and pro-enzymes.

27. The transformant of claim 21 wherein said second DNA segment encodes a plasminogen activator.

28. The transformant of claim 27 wherein said activator is human tissue plasminogen activator.

* * * * *